Figure 1:
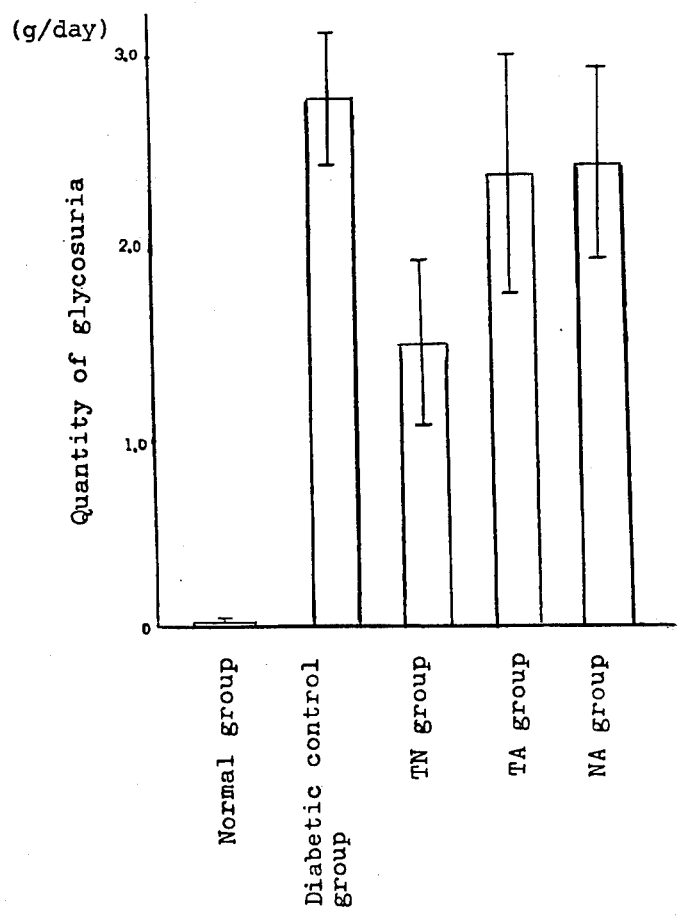

United States Patent [19]

Kawashima et al.

[11] 4,073,910

[45] Feb. 14, 1978

[54] METHOD FOR TREATMENT OF DIABETES

[75] Inventors: Hidetoshi Kawashima, Miyoshi; Shinzaburo Ohtake, Tokyo; Toru Fujimori, Kamakura; Isao Ohkawa, Hanno; Tetsuya Tajima, Nagareyama, all of Japan

[73] Assignee: Eisai Co., Ltd., Tokyo, Japan

[21] Appl. No.: 635,448

[22] Filed: Nov. 26, 1975

[51] Int. Cl.² .................................. A61K 31/455
[52] U.S. Cl. ................................................ 424/266
[58] Field of Search ................................. 424/266

[56] References Cited

FOREIGN PATENT DOCUMENTS 4,747,663  12/1972  Japan .................................. 424/266

OTHER PUBLICATIONS

Chem. Abstracts, vol. 46 (1952), 5209e; vol. 50, (1956), 4330f; vol. 67 (1967), 42195f; vol. 71 (1969), 79684y.
The Pharmacological Basis of Therapeutics, The Macmillan Company, N. Y., (p. 746).

Primary Examiner—Frederick E. Waddell
Attorney, Agent, or Firm—Wenderoth, Lind & Ponack

[57] ABSTRACT

Therapeutical treatment of diabetes by oral or parenteral administration of Vitamine E nicotinate which exhibits remarkable effects for treatment of diabetes without accompanying injurious side effect.

6 Claims, 5 Drawing Figures

METHOD FOR TREATMENT OF DIABETES

The present invention relates to a method for treatment of diabetes which comprises administering a therapeutically effective amount of nicotinic acid ester of Vitamine E (hereinafter referred to Vitamine E nicotinate) to a human suffering from diabetes.

The diabetes is an abnormal metabolism due to the deficiency of insulin activity, and is a typical one of the geriatric disorders containing cancer, heart disease and hypertensive disease as well. It has also been recently reported that juvenile diabetes tends to increase.

It is therefore a very important theme to treat the diabetes. However, there has not been found as yet a definitive method for treatment of the diabetes.

There has been conventionally used mainly insulin which is the pancreas hormone, as a medical treatment for diabetes. Further, there has appeared the preparation containing sulfonyl urea and the preparation containing biguanide, as, so called "oral medicine for diabetes" which is effective for oral administration.

It was reported in 1955 in West Germany that Carbutamide derived from sulfonyl urea has a remarkable effect for depressing a blood-sugar amount. [Refer to Achelis, J. D. et al. : Dtsch. med. Wschr.; 80, 1449 (1955)]. Since Tolbutamide was discovered in 1956, there have been developed a number of sulfonyl urea derivatives (hereinafter referred simply to "medicine SU") and biguanide derivatives (hereinafter referred simply to "medicine BG") as oral medicines for diabetes. The method for administration of these medicines is more simply than that of insulin, because these can be orally administered. The medicines have therefore come to be used universally as an epoch-making medicine for treatment of diabetes.

However, these medicines have not only a side-effect due to hypoglycemia, but also side-effects such as troubles of stomach and intestines, diarrhea and the like, when a large amount of the medicines is administered.

It was also reported that when University Group Diabetes Program (UDPG) in U.S. A studied a continuation effect by administration of Tolbutamide of the medicine SU or Phenformin of the medicine BG for 8 years, the number of deaths due to heart-blood vessel disorder in the group of oral administration amounts to 2.5 times, as compared with that of the placebo group [Refer to University Group Diabetes Program : Diabetes 19, (Supple 2), 747 (1970); and University Group Diabetes Program : Diabetes 19, (Supple 2), 789 (1970)].

In Japan, there were also reported the cases of serious hypoglycemia due to the oral hypoglycemic agent in diabetes such as the medicine SU and the like, whereby medicines were lately designated as powerful medicines, that is, separanda.

It is therefore desired eagerly to develope safe medicines which differ from the oral medicines for diabetes available in the market with respect to the mechanisms of action and which it is possible to administer for a long period of time without accompanying injurious side effects.

In view of the above mentioned facts, we studied various medicines, and found that Vitamine E nicotinate is safe and effective for treating diabetes, differing in the mechanism of action from that of the conventional medicine SU.

An object of the present invention is therefore to provide a novel method for treatment of diabetes.

Another object of the present invention is to provide a novel medicine for treatment of diabetes.

Other object of the present invention is to provide a medicine for treatment of diabetes which has low side effect and which it is possible to continuously administer for a long period of time.

The dl-α-tocopherol nicotinate (hereinafter referred simply to Compound TN), one of Vitamine E nicotinates to be used in the present invention, is a yellowish brown waxy material having a melting point of 35° - 40° C. The nicotinate is easily soluble in acetone, benzene, chloroform, ether and ethanol; and hardly soluble in water.

Compound TN can be prepared by any conventional esterification process.

dl-α-tocopherol is reacted with nicotinic anhydride or hydrochloride of nicotinic chloride which are reactive derivatives from nicotinic acid, in the presence of pyridine, to form the reaction product, which is then subjected to after-treatment, and finally purified through column chromatography to provide pure dl-α-tocopheryl nicotinate.

The medicine of the present invention is administered to a human suffering from diabetes, in a therapeutically effective amount, preferably a daily dose of from about 50 to 1200 mg.

There may be employed any administration form such as powder, tablet, capsule, injection and the like.

When said medicine is desired in a form of powder, it is prepared by adsorbing the compound on an inorganic excipient such as magnesium carbonate, silica anhydride [Syloid, Carplex (trade mark) etc.], synthetic aluminium silicate, calcium phosphate and the like, or an organic excipient such as lactose, corn-starch, cellulose [Avisel (trade mark) etc.] and the like.

When tablet or capsule is desired, the raw powder mentioned above is treated with conventional method to make tablet or capsule.

When injection is desired, the compound is treated with a non-ionic surfactant in accordance with a conventional process so as to give it a solubility in water and the resulting solution is processed to make an injection. Illustrative of non-ionic surfactants are for example, hydrogenated castor oil-ethylene oxide adducts [e. g. Nikkol HCO (trade mark), Emalex HC (trade mark)], fatty acid ester of sorbitan ethylene oxide adducts [e. g. Tween (trade mark)], alkyl phenol ethylene oxide adducts, fatty acid ester of sorbitan [e. g. Span (trade mark)] and the like. When injection is desired, there may also be employed conventional additives such as propylene glycol, dextrose and the like, which can be mixed with the compounds.

Toxicity of Compound TN employed in the present invention is illustrated as follows:

A. Test of Acute toxicity

Acute toxicity of Compound TN for males and females of mice rats were tested. The results of the tests are shown in the following Table 1.

It is confirmed from Table 1 that there is no case wherein the test animals died, even if large quantity (administerable maximum quantity) of Compound TN is administered, thus Compound TN is an exceedingly safe medicine.

Table 1

| Kind of Animal | Route | Sex | $LD_{50}$ (mg/Kg) |
|---|---|---|---|
|  | P.O. | Male | >15000 |

Table 1-continued

| Kind of Animal | Route | Sex | LD$_{50}$ (mg/Kg) |
|---|---|---|---|
| Rats | | Female | >15000 |
| | S.C. | Male | >15000 |
| | | Female | >15000 |
| | I.M. | Male | >10000 |
| | | Female | >10000 |
| | I.P. | Male | >2000 |
| | I.V. | Male | >250 |
| | | Female | >250 |
| Mice | P.O. | Male | >20000 |
| | | Female | >20000 |
| | S.C. | Male | >20000 |
| | | Female | >20000 |
| | I.M. | Male | >15000 |
| | | Female | >15000 |
| | I.P. | Male | >4000 |
| | I.V. | Male | >1000 |
| | | Female | >1000 |

NOTE:
P.O. Per oral
S.C. Subcutaneous
I.M. Intramusclar
I.P. Intraperitoneal
I.V. Intravenous B. Test of subacute and chronic toxicity The test was achieved in such a manner that Compound TN was administered continuously for three or six months to rats in an amount of 100 to 1000 mg/Kg, and to beagles in an amount of 100 mg/Kg. There could not be found the death case and the restraint of weight. Also, there could not be entirely recognized the appearance of the toxicity, from the hematological and blood biochemical searches, or histological searches of the main organs such as liver, kidney, speen, heart, lung, stomach, suprarenal body, spermary and the like.

C. Test for malformation

When Compound TN was oraly administered to pregnant mice or rats in an amount of 100 to 1200 mg/Kg, there could not be recognized any effects for mothers, foetuses and neonatal animals, whereby no malformation could be entirely found.

The following is a part of the pharmacological experiment for demonstrating the effect of the present invention.

EXPERIMENT

Effect of Vitamine E nicotinate on alloxan diabetes

I. Method for experiment

Experiments were carried out in six-week male wistar rats weighing approximately 180 g. Alloxan monohydrate was administered intraperitoneally to rat in a dose of 160 mg/Kg twice every other day. After 10 days, animals displaying abnormal quantity of glycosuria were selected as "diabetic" animals. Abnormality was arbitrarily determined as quantity of glycosuria for 24 hours over 0.5 g.

Total 32 alloxan diabetic rats were divided into four aliquot groups of every eight rats at random. To these rats, there were orally administered once a day for three weeks, 100 mg/Kg of dl-α-tocopheryl nicotinate (Compound TN), 80 mg/Kg of dl-α-tocopheryl acetate (hereinafter referred to Compound TA) equivalent to amount in Compound TN, 20 mg/Kg of nicotinic acid (hereinafter referred to Compound NA) equivalent to amount in Compound TN and 10 ml/Kg of 5% gum arabic as the control group of diabetes, respectively for each group. These rats were placed in the metabolism cage equiped with solid foods and drinking water. The foods were removed after 9 hours, and urine was collected from said rats for 24 hours.

In other experience, total 45 alloxan diabetic rats were divided into three groups of aliquot. To these rats, there were orally administered once a day for three weeks 100 mg/Kg of Compound TN, combination of 88 mg/Kg of Compound TA and 20 mg/Kg of Compound NA equivalent to amount in Compound TN, and 10 ml/Kg of 5% gum arabic, respectively, for each group. These rats were placed in the metabolism cages equiped with drinking water, and urine was collected for 12 hours. Blood was also collected in each case from the carotid artery of the rats under anesthesia.

for the urine and the plasma, the following biochemical tests were effected.

(a) Quantity of the blood-sugar and the glycosuria: Anthrone method. Morris, D. L: Science 107, 254 (1948)

(b) Quantity of urine-nitrogen: Diacetylmonoxime method, Miller, H. et al; Clinical Chemistry 11, 624 (1965)

(c) Quantity of cholesterol: Zak-Henly's method: Zak, B; Am. J. Clin, Chim, Path 27, 583 (1957)

(d) Quantity of neutral fat: Henry's modification method, Wadstrom, L. B; Clin, Chim Acta 4, 197 (1959)

(e) Quantity of NEFA: Laurell-TAC method; Laurell, S. et al; Clin. Chim. Acta 16, 57 (1967)

(f) phospholipid: Lee's method; Lee, L. M. Y; Clin. Chim. Acta 32, 25 (1971)

At the same time, the histological searches were achieved for livers, kidneys, pancreas, spleens and mesenteric lymphomas which were extirpated after the death caused by the blood-letting. II. Results of experiments Effect on the ingredients in urine FIGS. 1 and 2 show quantity of glycosuria in the urines for 24 hours and for 12 hours, respectively.

Figure 2:
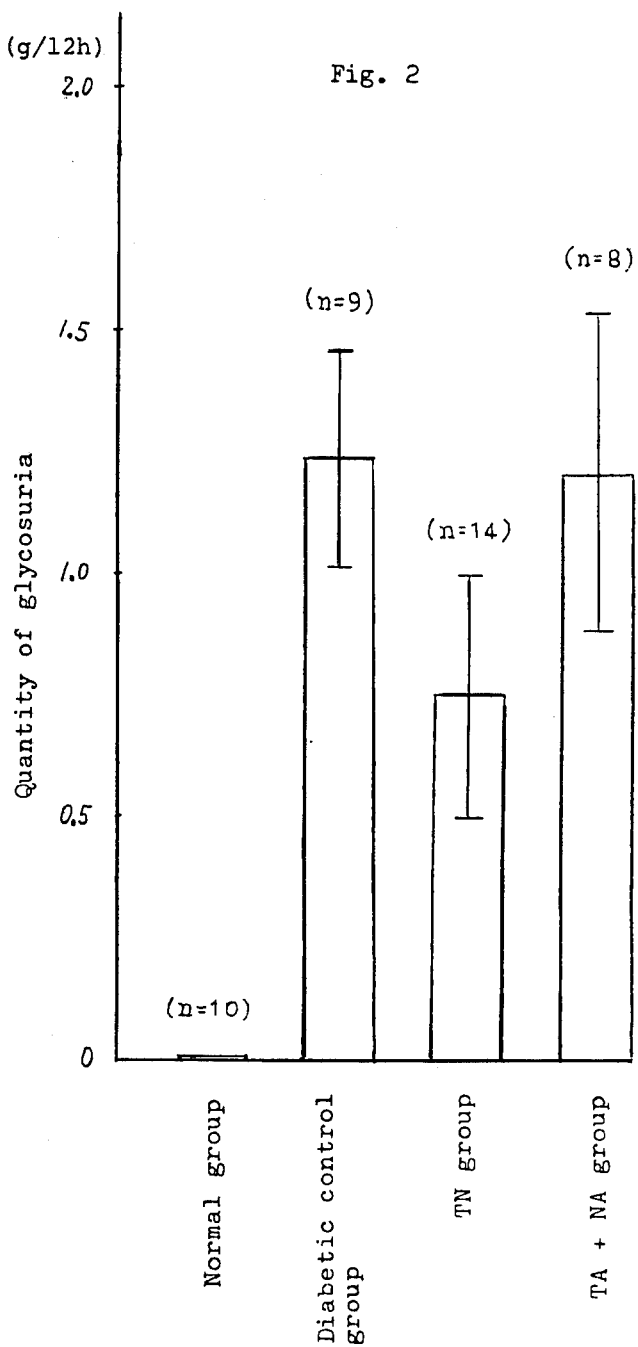

As shown in FIG. 1, the quantity of glycosuria in the urine of alloxan diabetic animals (P = 0.01) is clearly larger than that of the normal group of animals. Among the said animals, it was shown that the quantity of glycosuria in the Compound TN group is smaller than that of the diabetic control group by the mean value of 1.3 g/day (47%).

On the other hand, the restraining effect could not be found in the Compound TA and Compound NA groups. Such tendency as mentioned above is found also in FIG. 2. It is shown that the quantity of glycosuria in the alloxan diabetic control group is 1.24 g/12 hours in an average, and much larger than that in the normal group, while the quantity of glycosuria in the Compound TN group is 0.76 g/12 hours, the data of which are clearly reduced. On the contrary, the quantity of glycosuria in the Compounds TA + NA group is 1.22 g/12 hours. There could hardly be found the difference between the data in the alloxan diabetic control group and those in the compounds TA + NA group.

Effect on the blood-sugar

Figure 3:
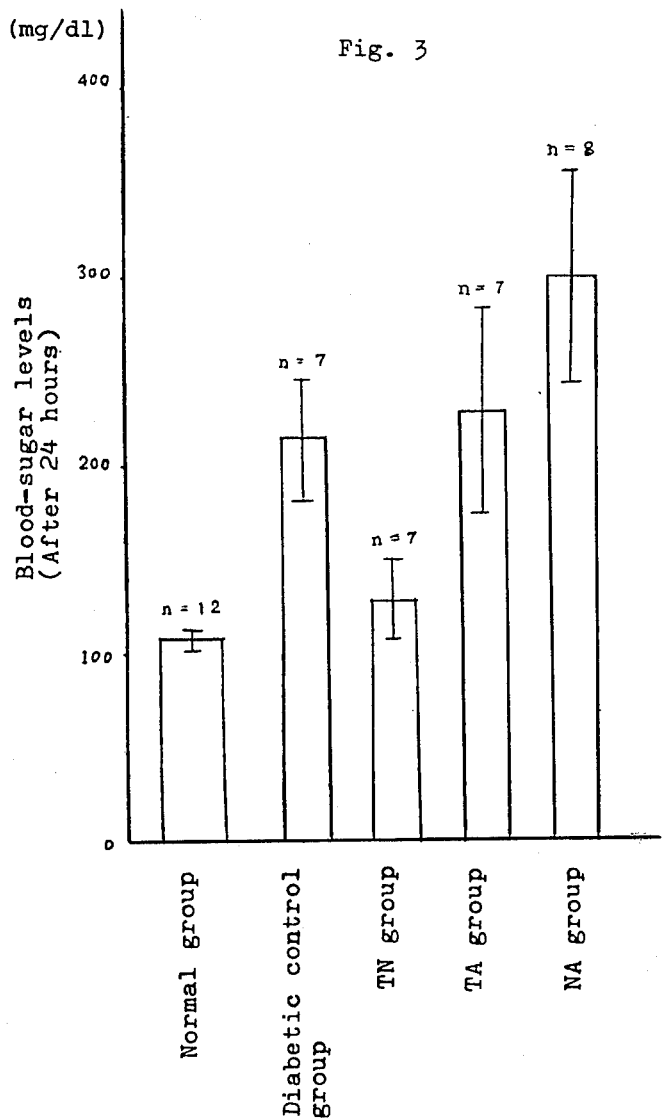
Figure 4:
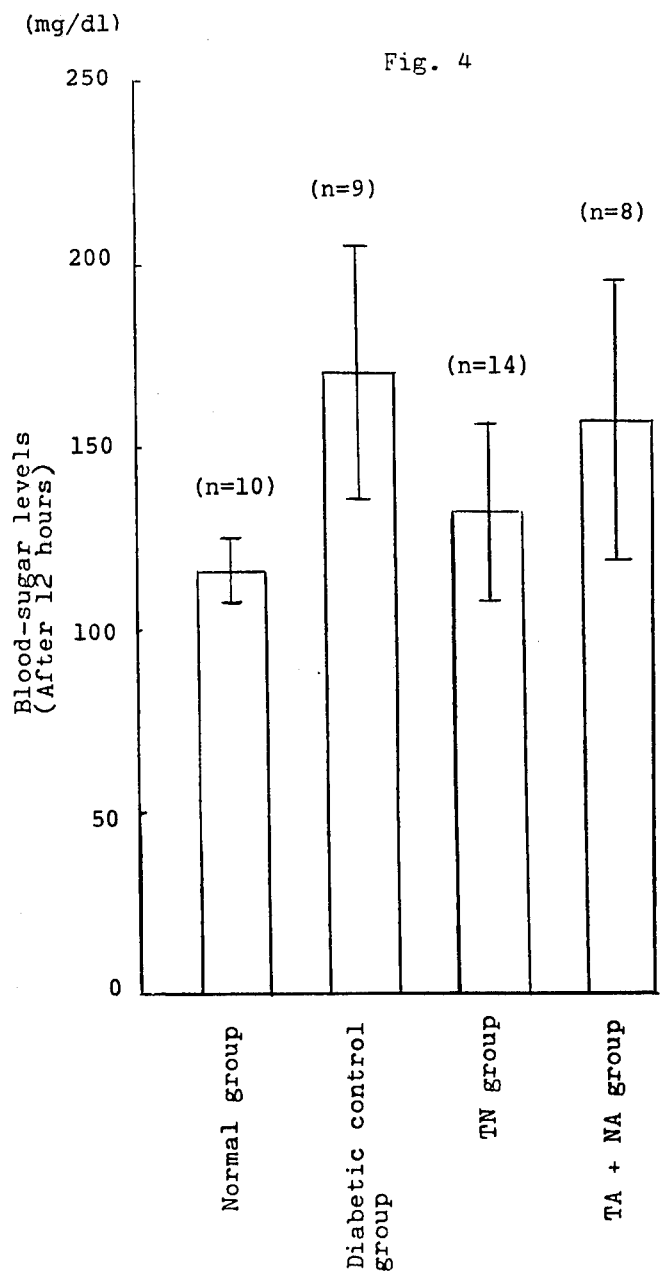

FIGS. 3 and 4 show the blood-sugar levels after 24 hours and 12 hours fasting, respectively. From FIGS. 3 and 4, it is obvious that the Compound TN of the present invention reduces significantly the quantity of the blood-sugar, as entirely same as the quantity of the glycosuria, and there can not be found the differences between the Compound TA group, the Compound NA group, the Compounds TA + NA group and the alloxan diabetic control group.

Effect on urinary volume

Figure 5:
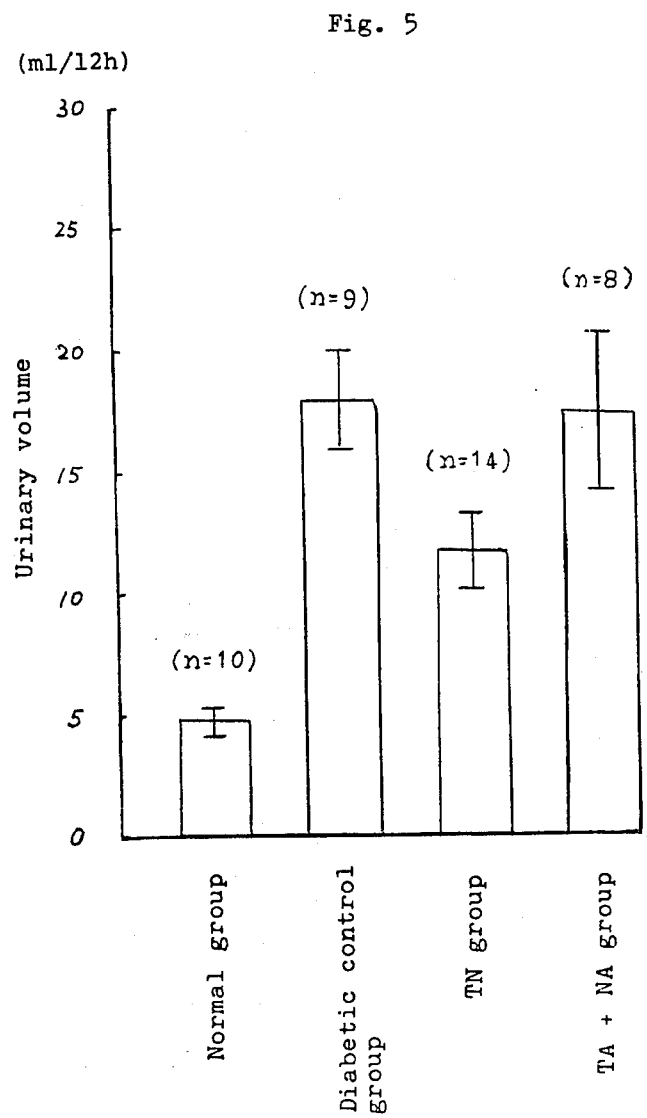

FIG. 5 shows the effect on urinary volume after 12 hours. It is obviously shown from FIG. 5 that urinary volume of the Compound TN group of the present invention reduces.

From the above-mentioned pharmacological experiments, there could not be found the difference among the Compound TA group, the Compound NA group and the diabetic control group with respect to the quantity of glycosuria, urinary volume, blood-sugar level and the like. However, the quantity of glycosuria, urinary volume, and blood-sugar level in Compound TN group of the present invention are small such as P = 0.05, as compared with those of the diabetic control group.

It is therefore concluded that Compound TN of the present invention has unique effect for treatment of alloxan-diabetes, because such effect can not be found in the Compound TA group, the Compound NA, and combination of the Compound TA and Compound NA group.

It was found from the above-mentioned animal tests that the Compound TN shows therapeutic effect for treatment of diabetes. The following are the clinical data for proving such animal tests.

Clinical Data

1. Subjects

There were selected 15 diabetics, whose blood-sugar values are 111-150 mg;, respectively. The diabetics are 56.8 years old in average, ranging from 49 to 65 years old. They consist of 10 males and 5 females.

2. Administration method and Experimental method

It was previously confirmed that the body weights of the diabetics are almost not varied during the continuation of dietetics.

There were orally administered a daily dose of six capsules for 8 weeks, each capsule containing 100 mg of the Compound TN.

Before and after the administration of the compound of the present invention, 50 g of sugar are orally administered to carry out glucose tolerance test. Quantities of blood-sugar were measured by means of Autoanalyzer with respect to the blood which was collected from the vein of the elbow. Further, quantities of insulin were measured, in accordance with Double antibody technic, before the glucose tolerance and after 30 minutes tolerance. From the following resulting quantities, value of $\Delta IRI/\Delta BS$ was calculated.

3. Data

Clinical data were listed in Table 2.

Table 2

| No. | Cases | Age | Sex | Obesity Index | Blood Sugar (1)* | | | | $\Delta IRI/\Delta BS$ (30 min.) | Blood Sugar (2)** | | | | $\Delta IRI\Delta BS$ (30 min.) |
|---|---|---|---|---|---|---|---|---|---|---|---|---|---|---|
| | | | | | FBS | 1 | 2 (hours) | 3 | | FBS | 1 | 2 (hours) | 3 | |
| 1 | S.A. | 65 | M | +14 | 126 | 214 | 204 | 134 | 0.34 | 114 | 196 | 185 | 136 | 0.39 |
| 2 | I.T. | 49 | M | +10 | 134 | 205 | 194 | 126 | 0.29 | 126 | 193 | 184 | 114 | 0.31 |
| 3 | H.M. | 54 | F | + 6 | 116 | 194 | 176 | 130 | 0.35 | 111 | 178 | 164 | 121 | 0.38 |
| 4 | B.I. | 61 | M | +18 | 146 | 236 | 216 | 194 | 0.25 | 124 | 198 | 195 | 179 | 0.36 |
| 5 | E.O. | 62 | F | +14 | 130 | 294 | 220 | 196 | 0.31 | 122 | 221 | 189 | 175 | 0.41 |
| 6 | K.Y. | 54 | F | + 8 | 121 | 214 | 203 | 175 | 0.34 | 119 | 201 | 178 | 154 | 0.39 |
| 7 | A.O. | 54 | M | + 9 | 133 | 257 | 217 | 183 | 0.28 | 123 | 205 | 185 | 171 | 0.33 |
| 8 | K.T. | 56 | M | + 7 | 114 | 196 | 201 | 155 | 0.33 | 104 | 174 | 186 | 141 | 0.42 |
| 9 | I.U. | 58 | M | + 5 | 118 | 198 | 192 | 147 | 0.36 | 110 | 164 | 154 | 105 | 0.45 |
| 10 | K.Y. | 59 | M | +16 | 129 | 249 | 220 | 185 | 0.27 | 114 | 211 | 179 | 154 | 0.44 |
| 11 | K.K. | 51 | F | +21 | 140 | 293 | 201 | 169 | 0.28 | 121 | 214 | 185 | 136 | 0.36 |
| 12 | Y.M. | 57 | M | +14 | 135 | 215 | 214 | 191 | 0.31 | 118 | 195 | 181 | 172 | 0.35 |
| 13 | O.H. | 57 | M | + 8 | 121 | 194 | 188 | 154 | 0.35 | 104 | 164 | 163 | 130 | 0.39 |
| 14 | H.A. | 60 | F | + 7 | 127 | 205 | 195 | 167 | 0.39 | 114 | 185 | 172 | 141 | 0.49 |
| 15 | G.I. | 55 | M | +13 | 132 | 233 | 214 | 186 | 0.33 | 121 | 197 | 190 | 153 | 0.45 |
| Mean | | 56.8 | | +11.3 | 128.1 | 226.5 | 203.7 | 166.1 | 0.319 | 116.3 | 193.1 | 179.3 | 145.5 | 0.394 |

*(1) Before administration,
**(2) After administration
Sexual distinction : M.....Male ; F.....Female ,
FBS : fasting blood sugar From the Table 2, the following are recognized.

a: Value of blood-sugar in an empty condition before administration of the compound of the present invention amounts to 128.1 mg% in average, while the corresponding value after the administration of the compound amounts to 116.3 mg% in average. There was clearly shown a tendency of improvement. $P < 0.001$.

b: As for increase after tolerance of 50 g of dextrose, it is clearly large before the administration, while there is clearly shown a tendency of a considerable decrease. That is to say, after one hour tolerance, the value was 226.5 mg% in average before administration, while the value was decreased to 193.1 mg% average after administration. After two hours tolerance, the value was 203.7 mg% in average before administration, while the value was decreased to 179.3 mg% in average after administration. Further, after three hours tolerance, the value was 166.1 mg% in average before administration, while the value was decreased to 145.5 mg% in average after administration. $P < 0.05$.

c: Value of $\alpha IRI/\alpha BS$ after 30 minutes tolerance is 0.319 in average before administration of the compound. The value shows clearly pattern of diabetes. However, the value of $\alpha IRI/\alpha BS$ amounted to 0.394 in average after administration of the compound of the present invention. These data show a tendency in the increase of the value. $P < 0.001$.

In all cases, there could hardly be found a tolerance with respect to the degree of adiposity.

From the above-mentioned clinical experiments, it is clear that the Compound TN of the present invention is effective as medicine for treatment of diabetes.

In addition, the Compound TN is one of Vitamine E derivatives, and accordingly, the Compound is a safe medicine without accompanying side effect such as hypoglycemia, as shown in the conventional medicine SU and medicine BG. Therefore, it is possible to administer the Compound for a long consecutive period of time.

The following examples are given to illustrate the medical preparation useful for administering the Compounds of the present invention, but should not be construed as limiting the invention.

EXAMPLE 1

Preparation of capsule

| Ingredient | Amount contained in each capsule (mg) |
| --- | --- |
| dl-α-tocopheryl nicotinate | 100.0 |
| silicic anhydride | 91.0 |
| cellulose acetate.phthalate | 9.0 |

The above ingredients are homogeneously mixed, and the resulting mixture is filled in a hard capsule made by gelatine.

EXAMPLE 2

Preparation of tablet

| Ingredient | Amount (mg) |
| --- | --- |
| dl-α-tocopheryl nicotinate | 105.0 |
| Silicic anhydride hydrate | 30.0 |
| Silicic anhydride | 17.0 |
| Cornstarch | 12.0 |
| Purified sugar | 20.0 |
| Calcium carboxymethyl cellulose | 10.0 |
| Crystalline cellulose (Avicel) | 41.0 |
| Polyvinyl pyrolidone (K-30) | 5.0 |
| Talc | 10.0 | dl-α-tocopheryl nicotinate is dissolved in acetone. The solution is then adsorbed to silicic anhydride hydrate, silicic anhydride and cornstarch. The adsorbed material is then dried. The resulting dried product is mixed with purified sugar, calcium carboxymethyl cellulose and crystalline cellulose. An aqueous solution of polyvinyl pyrolidone (K-30) is added, as a binding agent, to the mixture.

The resulting material is processed in accordance with a conventional manner to produce granules. Talc was added, as a lubricant, to the granules, and the whole was mixed homogeneously.

The product is finally treated to form tablets, so that each tablet may weight 250 mg.

EXAMPLE 3

Preparation of coated tablets for enteric use

Tablets are prepared in accordance with Example 2. The tablets are treated, in accordance with a conventional manner, with acetone solution containing cellulose acetate ·phthalate, so as to coat a film on the surface of the tablets.

EXAMPLE 4

Preparation of solution for injection

| Ingredient | Amount (mg) |
| --- | --- |
| dl-α-tocopheryl nicotinate | 100 |
| Solbitan monostearate (Alacel 60) | 40 |
| Benzyl alcohol | 40 |
| Hydrogenated castor oil polyoxyethylene 60 mol ether (HCO-60) | 140 |
| Sodium hydroxide | 0.12 |
| Distilled water sufficient to make up the total to 2 ml. | | dl-α-tocopheryl nicotinate, Alacel 60·HCO-60 and a part of distilled water for injection use are mixed with one another. To the mixture, there is then added benzyl alcohol, sodium hydroxide, and the remaining part of distilled water. After the whole is filtered, the filtrate is filled into a 2 ml ampoule, which is then sealed and sterilized.

EXAMPLE 5

Preparation of powders

| Ingredient | Amount (mg) |
| --- | --- |
| dl-α-tocopheryl nicotinate | 200 |
| Fine crystalline cellulose (Avicel) | 380 |
| Hydroxypropyl cellulose | 100 |
| Silicic anhydride | 200 |
| Starch | 120 |
| Total | 1000 | dl-α-tocopheryl nicotinate is dissolved in acetone. The solution is then adsorbed to silicic anhydride and starch, and the adsorbed material is dried. The dried product is further mixed with the other ingredients, and the mixture is treated, in accordance with a conventional manner, to prepare powders.

What is claimed is:

1. A method for treatment of diabetes comprising administering, a therapeutically effective amount of Vitamine E nicotinate to a human suffering from diabetes.

2. The method according to claim 1 which comprises administering a daily dose of from 50 to 1200 mg of Vitamine E nicotinate.

3. The method according to claim 1 which conmprises orally administering a therapeutically effective amount of Vitamine E nicotinate.

4. The method according to claim 1 which comprises administering by injection a therapeutically effective amount of Vitamine E nicotinate.

5. The method according to claim 1 which comprises orally administering a daily dose of from 50 to 1200 mg of Vitamine E nicotinate.

6. The method according to claim 1 which comprises administering by injection a daily dose of from 50 to 1200 mg of Vitamine E nicotinate.

* * * * *